(12) United States Patent
Lee et al.

(10) Patent No.: US 10,520,514 B2
(45) Date of Patent: Dec. 31, 2019

(54) METHOD FOR MONITORING POST-TRANSLATIONAL MODIFICATION OF PROTEIN

(71) Applicant: KOREA INSTITUTE OF SCIENCE AND TECHNOLOGY, Seoul (KR)

(72) Inventors: Soo-Hyun Lee, Seoul (KR); Ji-Yoon Kang, Seoul (KR); Min-Ho Kim, Seoul (KR); Yun-Kyung Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/696,302

(22) Filed: Sep. 6, 2017

(65) Prior Publication Data
US 2018/0217164 A1 Aug. 2, 2018

(30) Foreign Application Priority Data

Feb. 1, 2017 (KR) .................. 10-2017-0014324
Aug. 28, 2017 (KR) .................. 10-2017-0108858

(51) Int. Cl.
*G01N 33/68* (2006.01)
*G01N 27/02* (2006.01)
(Continued)

(52) U.S. Cl.
CPC ..... *G01N 33/6896* (2013.01); *G01N 21/6428* (2013.01); *G01N 27/021* (2013.01);
(Continued)

(58) Field of Classification Search
CPC ......... G01N 33/6896; G01N 33/54326; G01N 33/54373; G01N 21/6428; G01N 21/76; G01N 27/021
See application file for complete search history.

(56) References Cited

U.S. PATENT DOCUMENTS 5,585,241 A * 12/1996 Lindmo ................. G01N 15/14
    435/6.11
2002/0132260 A1 * 9/2002 Erlander ............. C12Q 1/6816
    435/6.14
(Continued)

FOREIGN PATENT DOCUMENTS

WO    WO 2016/193980 A1    12/2016

OTHER PUBLICATIONS

Sophia Doll et al., "Mass Spectrometry-Based Detection and Assignment of Protein Posttranslational Modification", ACS Chemical Biology, 2015, pp. 63-71, vol. 10.
(Continued)

*Primary Examiner* — Melanie Brown
(74) *Attorney, Agent, or Firm* — Rabin & Berdo, P.C.

(57) ABSTRACT

According to a method for monitoring post-translational modifications of protein is provided, a first microbead by binding a protein antibody to a base bead is provided. A second microbead by binding a target protein having a first post-translational modification or a second post-translational modification, which are inversely proportional to each other, to the protein antibody of the first microbead, is provided. A third microbead by binding the second microbead to a first post-translational modification antibody is provided. A fourth microbead by binding the second microbead to a second post-translational modification antibody is provided. Impedances of the third and fourth microbeads are measured. A ratio of a first difference, between the impedances of the third microbead and a reference impedance, to a second difference, between the impedances of the fourth microbead and the reference impedance, is obtained.

8 Claims, 6 Drawing Sheets

(51) Int. Cl.
*G01N 21/64* (2006.01)
*G01N 33/543* (2006.01)
*G01N 21/76* (2006.01)

(52) U.S. Cl.
CPC . *G01N 33/54326* (2013.01); *G01N 33/54373* (2013.01); *G01N 21/76* (2013.01); *G01N 2333/47* (2013.01); *G01N 2440/38* (2013.01); *G01N 2800/2821* (2013.01); *G01N 2800/52* (2013.01)

(56) References Cited

U.S. PATENT DOCUMENTS

| | | | |
|---|---|---|---|
| 2006/0223130 A1 | 10/2006 | Yang et al. | |
| 2008/0020409 A1* | 1/2008 | Pawlak | G01N 33/567 435/7.23 |
| 2010/0331200 A1 | 12/2010 | Gordon et al. | |
| 2016/0060687 A1* | 3/2016 | Zhu | C12Q 1/6837 506/2 |

OTHER PUBLICATIONS

Jose O. Esteves-Villanueva et al., "Electrochemical detection of anti-tau antibodies binding to tau protein and inhibition of GSK-3β-catalyzed phosphorylation", Analytical Biochemistry, 2016, pp. 55-62, vol. 496.
Korean Office Action dated Dec. 10, 2018.
International Search Report of PCT/KR2017/009793 dated Sep. 7, 2017.
Roland Brandt et al., "Tau alteration and neuronal degeneration in tauopathies: mechanisms and models", Biochimica et Biophysica Acta, 2005, pp. 331-354, vol. 1739.
Tania F. Gendron et al., "The role of tau in neurodegeneration", Molecular Neurodegeneration, Mar. 2009, pp. 1-19, vol. 4, No. 13.

* cited by examiner

METHOD FOR MONITORING POST-TRANSLATIONAL MODIFICATION OF PROTEIN

The present application claims priority to and the benefit of Korean Patent Application No. 10-2017-0014324, filed on Feb. 1, 2017 and No. 10-2017-0108858, filed on Aug. 28, 2017, the disclosures of which are incorporated by reference herein in their entirety.

BACKGROUND

1. Field

Example embodiments of the inventive concept relate to a method for monitoring tau protein. More particularly, example embodiments of the inventive concept relate to a method for monitoring post-translational modifications of proteins.

2. Description of the Related Art

Abnormal tau aggregation is a major feature in Alzheimer's disease (AD) and many other neurodegenerative diseases (collectively, called tauopathies). (Brandt R, Hundelt M, Shahani N(2005) Tau alteration and neuronal degeneration in tauopathies: mechanisms and models. Biochimica. et biophysica. acta. 1739: 331-354) In healthy nerves, the tau stabilizes microtubules by promoting growth from axons and polarization of neurons. When pathologically hyperphosphorylated, the tau is detached from the microtubule to produce insoluble aggregates. (Gendron T F, Petrucelli L (2009) The role of tau in neurodegeneration. Mol. Neurodegener. 4: 13)

In the brains suffering from the Alzheimer's disease, abnormally hyperphosphorylated tau and its aggregates are observed as an onset. Thus, excessive phosphorylation is generally considered to be the cause of tau aggregation.

Recent studies have shown that hyperphosphorylation and O-glycosylation in several post translational modifications (PTMs) of tau proteins are inversely related to each other.

Therefore, if the degree of phosphorylation of tau protein and the degree of O-glycosylation can be measured, it can be a basis for judging the progression rate or prognosis of the disease. It can also be used as a tool for verifying the effect of new drug development.

Thus, when the tau protein can be accurately detected, it can be helpful in judging the prognosis of neurodegenerative diseases or judging the therapeutic effect.

Currently, tau PET is known as a test method for tau protein. However, since tau PET requires oral administration of a radiation substance (contrast agent), there are problems about limitation of inspection interval and high cost. In addition, when a blood test or the like is to be used, the concentration of tau protein is low, so that reliable and accurate detection is difficult due to difficulty of quantitative analysis.

Referring to recent researches, absolute quantity of tau protein or phosphorylated tau protein does not coincide with state of a patient because each patient may have different amounts of proteins. Thus, even if absolute quantity of tau protein or phosphorylated tau protein may be measured, it may be hardly used for index for diagnosis or prognosis of a patient.

SUMMARY

Exemplary embodiments provide a method for monitoring post-translational modifications of proteins capable of improving reliability and easy performing.

According to an exemplary embodiment, a method for monitoring post-translational modifications of protein is provided. In the method, a first microbead by binding a protein antibody to a surface of a base bead is provided. A second microbead by binding a target protein having a first post-translational modification or a second post-translational modification, which are inversely proportional to each other, to the protein antibody of the first microbead, is provided. A third microbead by binding the second microbead to a first post-translational modification antibody that selectively binds to a first post-translational modification of the target protein is provided. A fourth microbead by binding the second microbead to a second post-translational modification antibody that selectively binds to a second post-translational modification of the target protein is provided. Impedances of the third microbead and the fourth microbead are measured, respectively. A ratio of a first difference to a second difference is obtained. The first difference is difference between the impedance of the third microbead and a reference impedance, and the second difference is difference between the impedance of the fourth microbead and the reference impedance.

In an exemplary embodiment, the target protein may be tau protein.

In an exemplary embodiment, the first post-translational modification may be phosphorylated tau protein, and the second post-translational modification may be O-glycosylated tau protein.

In an exemplary embodiment, the base bead may be a magnetic bead.

In an exemplary embodiment, the reference impedance may be impedance of the first microbead.

In an exemplary embodiment, the reference impedance may be impedance of the second microbead.

In an exemplary embodiment, in obtaining the ratio of the first difference to the second difference, the ratio of the first difference to the second difference at a first time point may be obtained, the ratio of the first difference to the second difference at a second time point which is different from the first time point may be obtained, and the ratio of the first time point with the ratio of the second time point may be compared.

In an exemplary embodiment, measuring the impedances of the third microbead and the fourth microbead may be performed with the third microbead or the fourth microbead being disposed between the first electrode and the second electrode.

According to an exemplary embodiment, a method for monitoring post-translational modifications of protein is provided. In the method, a first post-translational modification of a target protein is combined with a first post-translational modification antibody capable of being selectively combined with the first post-translational modification to prepare a first post-translational modification medium. A second post-translational modification of the target protein is combined with a second post-translational modification antibody capable of being selectively combined with the second post-translational modification to prepare a second post-translational modification medium. The second post-translational modification is inversely proportional to the first post-translational modification. A first measured value of the first post-translational modification medium for a physical characteristic or a chemical characteristic, which varies depending on degree of the first post-translational modification and the second post-translational modification is obtained. A second measured value of the second post-translational modification medium for the physical characteristic or the chemical characteristic is obtained. A ratio of a first difference to a second difference is obtained. The first difference is a difference between the first measured value and a reference value, and the second difference is a difference between the second measured value and the reference value.

In an exemplary embodiment, each of the first measured value and the second measured value is impedance.

In an exemplary embodiment, each of the first post-translational modification medium and the second post-translational modification medium includes a fluorescence or a chemiluminescence. Each of the first measured value and the second measured value is a measured value of an optical characteristic varying depending on an amount of the fluorescence or the chemiluminescence.

According to the example embodiments of the present inventive concept, physical characteristics or chemical characteristics, which vary depending on amounts of the post-translational modified proteins having an inversely proportional relationship with each other are respectively measured, and the change in the ratio may be used as an index, so that reliable detection results can be obtained as to whether or not the protein corresponding to the desired post-translational modification is increased or decreased.

It is to be understood that both the foregoing general description and the following detailed description are exemplary and explanatory and are intended to provide further explanation of the invention as claimed

BRIEF DESCRIPTION OF THE DRAWINGS

The above and other features of the inventive concept will become more apparent by describing in detail example embodiments thereof with reference to the accompanying drawings, in which.

DETAILED DESCRIPTION

Figure 1:
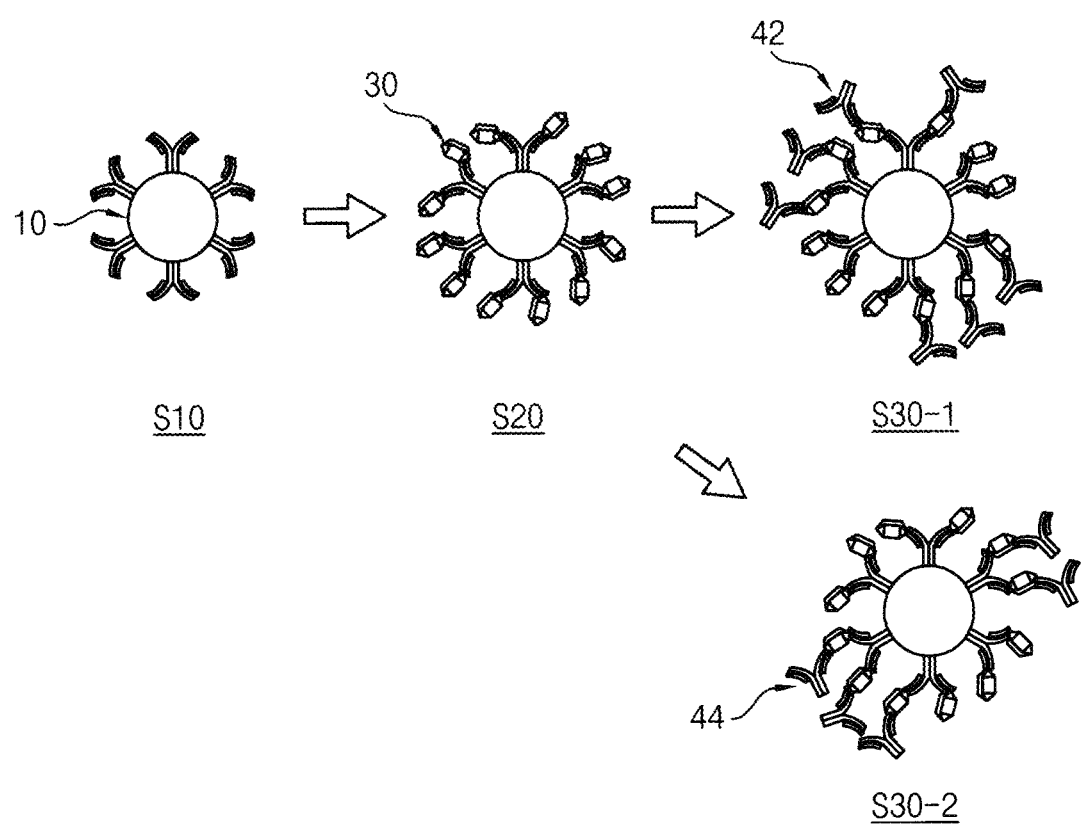
FIG. 1 is a flowchart briefly illustrating a method for monitoring post-translational modifications of proteins according to an example embodiment of the inventive concept.

Example embodiments are described more fully hereinafter with reference to the accompanying drawings. The inventive concept may, however, be embodied in many different forms and should not be construed as limited to the example embodiments set forth herein. In the drawings, the sizes and relative sizes of layers and regions may be exaggerated for clarity. It will be understood that, although the terms first, second, third etc. may be used herein to describe various elements, components, regions, layers, patterns and/or sections, these elements, components, regions, layers, patterns and/or sections should not be limited by these terms. These terms are only used to distinguish one element, component, region, layer pattern or section from another region, layer, pattern or section. Thus, a first element, component, region, layer or section discussed below could be termed a second element, component, region, layer or section without departing from the teachings of example embodiments.

Example embodiments are described herein with reference to cross sectional illustrations that are schematic illustrations of illustratively idealized example embodiments (and intermediate structures) of the inventive concept. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of the inventive concept.

The terminology used herein is for the purpose of describing particular example embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A Method for Monitoring Post-Translational Modifications of Proteins

FIG. 1 is a flowchart briefly illustrating a method for monitoring post-translational modifications of proteins according to an example embodiment of the inventive concept.

Referring to FIG. 1, first, a microbead 10 combined with a protein antibody 20 capable of binding to a target protein is provided (S10).

For example, the microbead (base bead) 10 may be a magnetic bead made of metal, polymer or the like. For example, a diameter of the microbead 10 may be from 1 μm (micrometer) to 5 μm, but it is not limited thereto. The microbead 10 having a diameter of 1 μm or more can be used according to an antibody and a detection system.

At least one protein antibody 20 may be bounded to a surface of the microbead 10. The microbead can be tosylated, amine treated or carboxylated, so that the microbead 10 can bind to the antibody.

The protein antibody 20 can bind to a target protein. For example, the target protein for detection may be a tau protein. As the antibody for binding to the tau protein, known ones can be used.

The microbead 10 combined with the protein antibody 20 may be referred to as a first microbead.

And then, the target protein 30 is bound to the protein antibody 20 of the microbead 10 (S20). Appropriate incubation and washing may be performed after mixing the microbead 10 and the target protein 30, in order to bind the target protein 30 to the protein antibody 20. The target protein 30 may be tau and may be obtained from a body fluid comprising at least one of blood, blood plasma, blood serum, saliva, urine, tears, nasal mucus or cerebral spinal fluid (CSF).

The microbead 10 combined with the target protein 30 may be referred to as a second microbead.

And then, post-translational modification antibody capable of selectively binding according to post-translational modifications of the target protein 30 is provided, and the target protein 30 and the post-translational modification antibody are combined. (S30-1, S30-2)

For example, the target protein 30 has at least two post-translational modifications (first post-translational modification and second post-translational modification), and at least two of the post-translational modified antibodies corresponding to each post-translational modifications may be provided.

Figure 4:
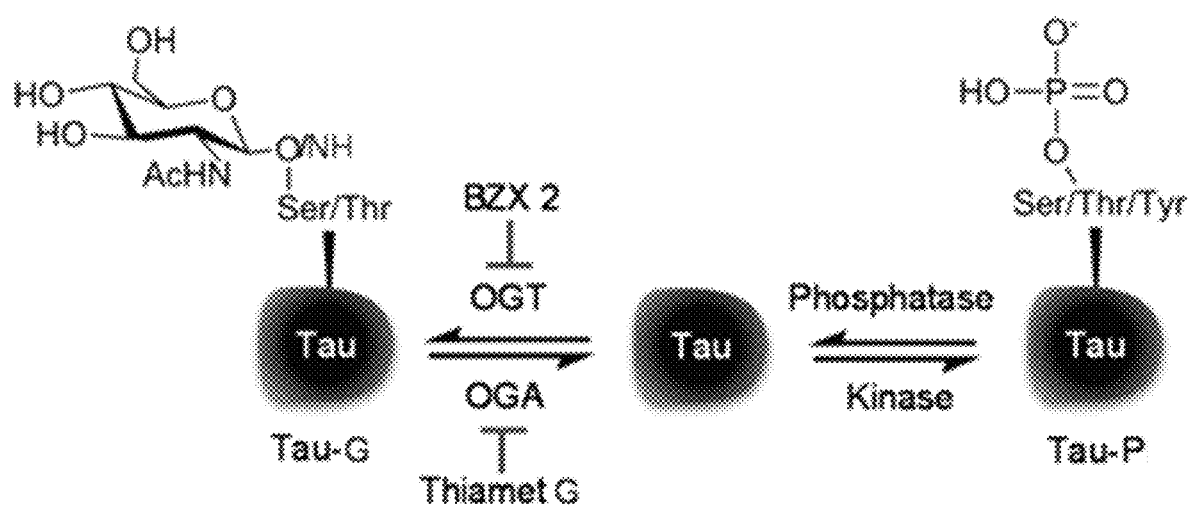
FIG. 4 is a view illustrating reactions by which tau proteins can be O-glycosylated or phosphorylated.

For example, the target protein 30 may be phosphorylated tau or O-glycosylated tau. For example, tau proteins can be O-glycosylated or phosphorylated by the reactions as illustrated in FIG. 4, which are known to have a trade-off between them.

Thus, the post-translational modified antibodies includes a first post-translational modification antibody 42 capable of selectively binding to phosphorylated tau and a second post-translational modification antibody 44 capable of selectively binding to O-glycosylated, respectively.

Accordingly, the number or proportion of the post-translational modified antibodies that bind to the target protein 30 may vary depending on the degree of post-translational modification of the target protein 30, which can be measured by impedance change of the microbead.

The microbead S30-1 after binding with the first post-translational modification antibody 42 may be referred to as a third microbead. The microbead S30-2 after binding with the second post-translational modification antibody 44 may be referred to as a fourth microbead.

According to an example embodiment of the present invention, impedance of the microbead S20 after binding with the target protein, impedance of the microbead S30-1 after binding with the first post-translational modification antibody 42 and impedance of microbead S30-2 after binding with the second post-translational modification antibody 44 are measured, respectively. In order to measure the impedance of the microbeads, a biosensor may be used. Preferably, the biosensor may have an electrode structure having a nanogap. This will be described later.

The microbead S20 after binding with the target protein and the microbead after binding with the post-translational modification antibody may have impedances different from each other. For example, the impedance of the microbead after binding with the post-translational modification antibody is smaller than measured impedance of the microbead S20 after binding with the target protein. In addition, when the number of post-translational modified antibodies bound to the target protein increases, the difference in impedance of the microbeads (before binding—after binding) may increase.

Thus, a difference between the measured impedance of the microbead S20 after binding with the target protein and the impedance of the microbead after binding with the post-translational modification antibody may be a marker for the degree of post-translational modification of the target protein. However, protein amount may largely vary depending on each patient or measuring time. Thus, only absolute quantity of phosphorylated tau protein may be hardly used for index for diagnosis or prognosis of a patient.

Thus, in the present invention, impedance variation by the O-glycosylated tau having a specific relationship with the phosphorylated tau, specifically in inverse relationship, is measured, and then a reliable measurement result can be obtained as to whether or not the phosphorylated tau is increased or decreased by using a ratio between the impedance variation by the phosphorylated tau and the impedance variation by the O-glycosylated tau as an index. The ratio may be used for index for diagnosis or prognosis of a patient.

In some example embodiment, the impedance of the microbead S20 after binding with the target protein may be used as reference impedance, but this is exemplary. In some example embodiment, the impedance of the microbead after binding with the protein antibody 20 may be used as reference impedance.

Therefore, the impedances of the post-translational modified proteins having an inversely proportional relationship with each other are respectively measured, and the change in the ratio may be used as an index, so that reliable detection results can be obtained as to whether or not the protein corresponding to the desired post-translational modification is increased or decreased.

The protein antibody and the post-translational modification antibody, those currently available on the market can be used.

For example, as an antibody capable of selectively binding to phosphorylated tau, Phospho-Tau(Ser202, Thr205) Antibody(AT8) MN1020(Thermo Fisher), Anti-Tau(phosphor S396) antibody [EPR2731]/ab109390(abcam), Phospho-Tau(ser202_ Antibody, #11834)(Cell signaling), Phospho-Tau(ser396) (PHF13) Mouse mAb, #9632(Cell signaling), etc. may be used. In addition, An antibody capable of selectively binding to O-glycosylated tau (an antibody capable of binding to various O-glycosylated proteins including tau), O-GlcNAc(CTD110.6) Mouse mAB, #9875(Cell signaling), etc. may be used. However, they are not limited thereto.

Figure 2:
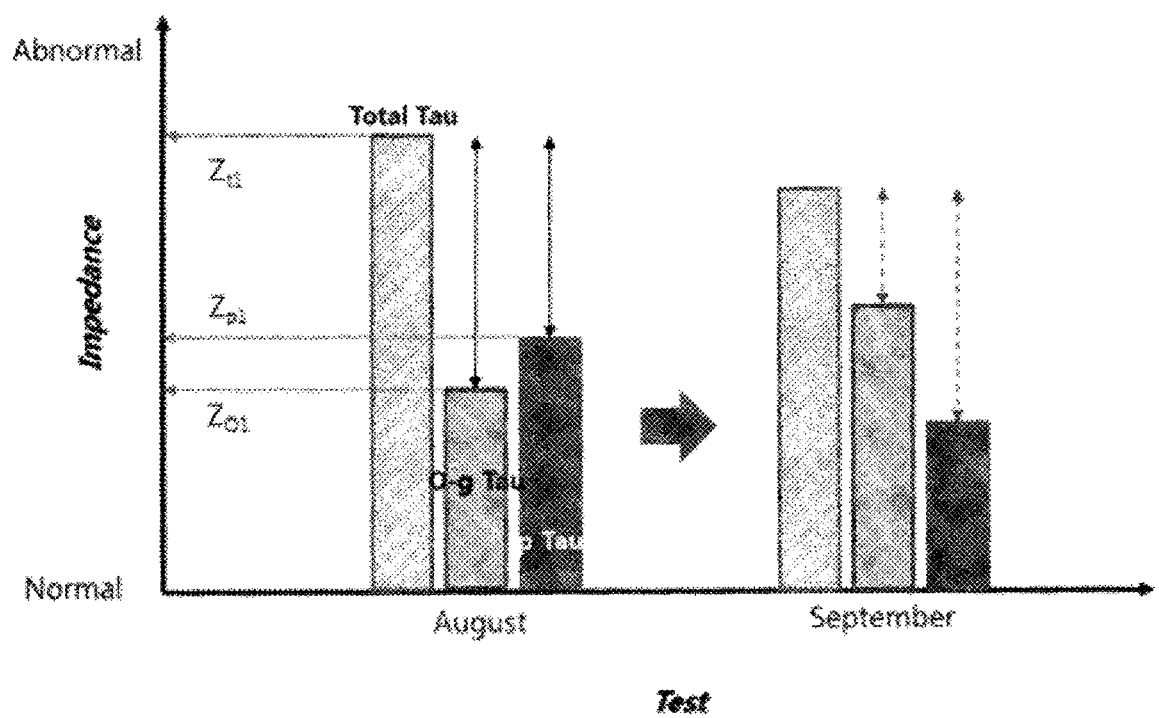
FIG. 2 is a graph illustrating a step of determining whether a target protein is increased or decreased by using a method for monitoring post-translational modification of proteins according to an embodiment of the present invention.

FIG. 2 is a graph illustrating a step of determining whether a target protein is increased or decreased by using a method for monitoring post-translational modification of proteins according to an embodiment of the present invention.

Referring to FIGS. 1 and 2, at a first time point, a sample containing tau protein is taken from a patient in August as an example, and the impedance of the microbead in step S20 is measured. The microbead in step S20 is bound to a first post-translational modification antibody capable of binding to phosphorylated tau (P Tau) and a second post-translational modification antibody capable of binding to O-glycosylated tau (O-g Tau), respectively. And then, impedance is respectively measured. Thereby, the impedance Zt1 of the reference microbead (microbead not bound to the post-translational modification antibody), the impedance Zp1 of the microbead binding with the first post-translational modification antibody, and the impedance Zo1 of the microbead binding with the second post-translational modification antibody are measured, respectively. Thus, impedance reduction (Zt1−Zp1) due to the phosphorylated tau and impedance reduction (Zt1−Zo1) due to the O-glycosylated tau can be obtained.

Next, at a second time point, a sample containing tau protein is taken from the patient in September as an example, and the impedance of the microbead in step S20 is measured. The microbead in step S20 is bound to a first post-translational modification antibody capable of binding to phosphorylated tau (P Tau) and a second post-translational modification antibody capable of binding to O-glycosylated tau (Og Tau), respectively. And then, impedance is respectively measured. Thereby, the impedance Zt2 of the reference microbead (microbead not bound to the post-translational modification antibody), the impedance Zp2 of the microbead binding with the first post-translational modification antibody, and the impedance Zo2 of the microbead binding with the second post-translational modification antibody are measured, respectively. Thus, impedance reduction (Zt2−Zp2) due to the phosphorylated tau and impedance reduction (Zt2−Zo2) due to the O-glycosylated tau can be obtained.

Considering that it is difficult to directly quantitatively measure the phosphorylated tau as described above, reliability of determining the increase or decrease of phosphorylated tau by comparing the impedance reduction (Zt1−Zp1) due to the phosphorylated tau at the first time point and the impedance reduction (Zt2−Zp2) due to the phosphorylated tau at the second time point, is low However, since the phosphorylated tau has a mutually exclusive (inverse) relationship with the O-glycosylated tau, comparing the ratios of the two can be a reliable detection method.

For example, at the first time point, the ratio of phosphorylated tau to O-glycosylated tau can be expressed as Zt1−Zp1/Zt1−Zo1 and at the second time point can be expressed as Zt2−Zp2/Zt2−Zo2.

Therefore, it is possible to determine whether the phosphorylated tau is increased or decreased according to the direction (increase or decrease) of the change in the ratio of the phosphorylated tau to the O-glycosylated tau. Consequently, it can be an indicator of progression or improvement of disease associated with phosphorylated tau. In addition, it is possible to determine the progression or the speed or degree of the disease according to magnitude of the change.

In the present embodiment, the above method was used using the detection or measurement of phosphorylated tau protein. However, the present invention is not limited thereto, and the present invention can be used for detection or measurement of all proteins with post-translational modifications of mutually exclusive relationship similar to tau protein.

In the embodiment, measuring impedance is used for obtaining the index, however, exemplary embodiments of the present inventive concept are not limited thereto. According to an exemplary embodiment, other physical characteristics or chemical characteristics may be used for obtaining similar index.

For example, a post-translational modification antibody may be combined with fluorescence. When a microbead is combined with the post-translational modification antibody combined with fluorescence, the microbead, which may be referred as a post-translational modification medium, may include a different amount of fluorescence depending on degree of post-translational modification of a target protein.

Thus, optical characteristics such as a light intensity in response to a light having a specific wavelength, an intensity of a reflective light or the like may be measured for a first post-translational modification medium combined with a first post-translational modification antibody, and a second post-translational modification medium combined with a second post-translational modification antibody to obtain a first measured value for the first post-translational modification medium, and a second measured value for the second post-translational modification medium. The first measured value may be compared with a reference value to obtain a value, which may be a difference between the first measured value and the reference value, corresponding to variation of the optical characteristic due to a first post-translational modification. The second measured value may be compared with a reference value to obtain a value, which may be a difference between the second measured value and the reference value, corresponding to variation of the optical characteristic due to a second post-translational modification.

In an exemplary embodiment, the fluorescence may be combined with the post-translational modification antibody before the post-translational modification antibody is combined with the target protein of the microbead. However, in another exemplary embodiment, the fluorescence may be combined with the post-translational modification antibody after the post-translational modification antibody is combined with the target protein of the microbead.

In another exemplary embodiment, chemiluminescence may be used instead of the fluorescence.

A Method of Manufacturing a Biosensor Having a Nanogap

FIGS. 3A, 3B, 3C, 3D, 3E, 3F and 3G are cross-sectional views illustrating a method of manufacturing a biosensor having a nanogap usable in a method for monitoring post-translational modification of proteins according to an embodiment of the present invention.

Figure 3A:
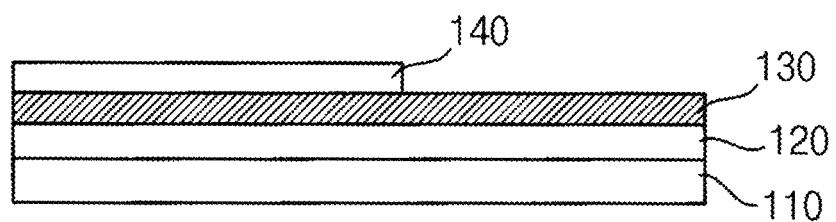
FIGS. 3A, 3B, 3C, 3D, 3E, 3F and 3G are cross-sectional views illustrating a method of 5 manufacturing a biosensor having a nanogap usable in a method for monitoring post-translational modification of proteins according to an embodiment of the present invention.

Referring to FIG. 3A, an inorganic insulating layer 120 is formed on the base substrate 110. A first metal layer 130 is formed on the inorganic insulating layer 120. A first photoresist pattern 140 is formed on the first metal layer 130.

For example, the base substrate 110 may include silicon, glass, quartz, polymer, and the like.

For example, the inorganic insulating layer 120 may include an insulating material such as silicon oxide or silicon nitride.

The first metal layer 130 may include gold, silver, platinum, chromium, copper, titanium, alloys thereof, and the like. The first metal layer 130 may have a single layer or a stacked structure of different metal layers. In some example embodiments, the first metal layer 130 may have a two-layer structure of chrome/gold.

The first photoresist pattern 140 partially covers the first metal layer 130 to partially expose an upper surface of the first metal layer 130.

Figure 3B:
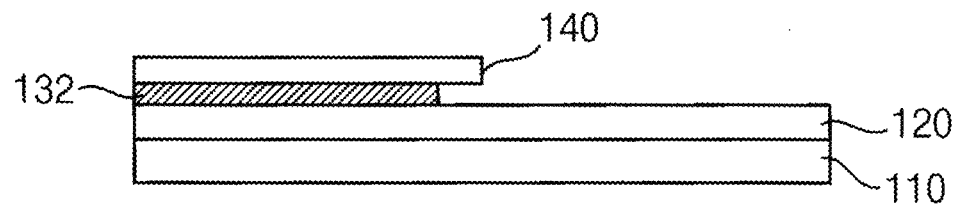

Referring to FIG. 3B, the first metal layer 130 is etched to form a first electrode 132. The etching process is performed by isotropic etching by wet etching. Accordingly, the first electrode 132 forms an undercut with respect to the first photoresist pattern 140.

Figure 3C:
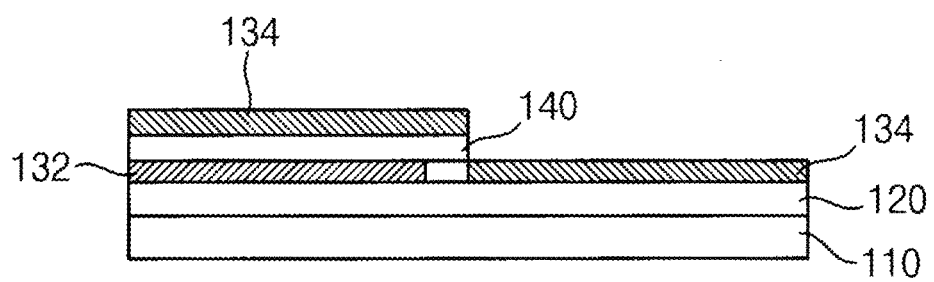

Referring to FIG. 3C, a second metal layer 134 is formed on an exposed upper surface of the first photoresist pattern 140 and the inorganic insulating layer 120. The second metal layer 134 may be formed by deposition such as sputtering, atomic beam evaporation, or the like, and is not formed under the first photoresist pattern 140 having undercuts.

The second metal layer 134 may include gold, silver, platinum, chromium, copper, titanium, alloys thereof, and the like. The second metal layer 134 may have a single layer or a laminated structure of different metal layers. In some example embodiment, the second metal layer 134 may have a two-layer structure of chrome/gold.

Figure 3D:
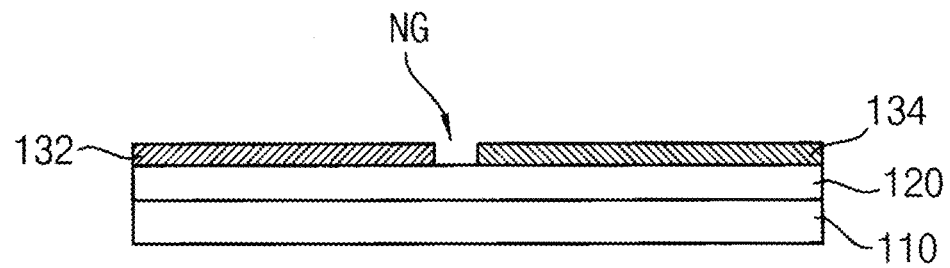

Referring to FIG. 3D, the first photoresist pattern 140 and the second metal layer 134 disposed thereon are removed. Therefore, a nanogap NG may be formed between the first electrode 132 and the remaining second metal layer 134.

Since the nanogap is not formed by etching using a mask after exposure of a photolithography process, but is formed by lift-off after formation of the undercut, so that it can be made smaller than a critical dimension of the photolithography process, and a wafer-level large area process is possible.

Figure 3E:
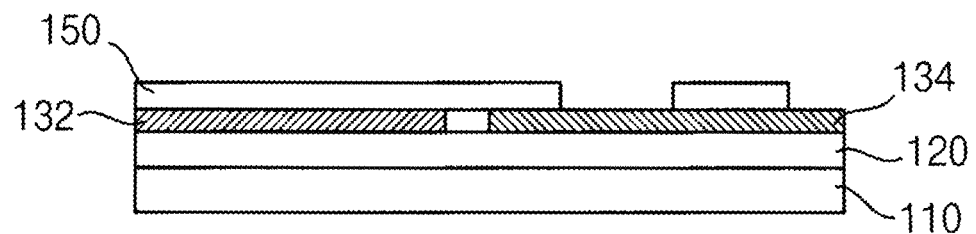

Referring to FIG. 3E, a second photoresist pattern 150 is formed on the first electrode 132 and the remaining second metal layer 134. The second photoresist pattern 150 may cover the nanogap NG and partially expose the second metal layer 134.

Figure 3F:
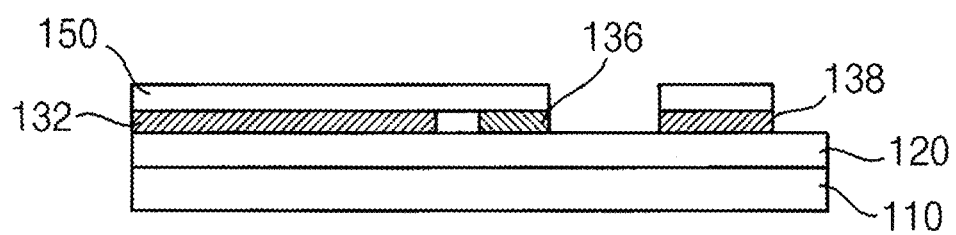

Referring to FIG. 3F, the remaining second metal layer 134 is etched using the second photoresist pattern 159 as a mask to form a second electrode 136 and a contact portion 138.

Figure 3G:
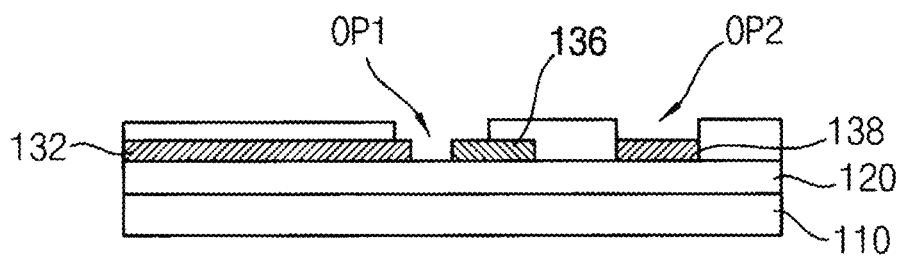

Referring to FIG. 3G, an organic insulating layer 160 is formed on the first electrode 132, the second electrode 136, and the contact portion 138. The organic insulating layer 160 may have a first opening OP1 for exposing the nanogap NG and a second opening OP2 for exposing the contact portion 138.

A microbead having magnetism may be inserted in the first opening OP1 of the biosensor for sensing. For example, when the microbead is provided on the biosensor and a magnetic substance is disposed under the biosensor, an attraction force in a vertical direction is applied to the microbead by the magnetic substance. When the magnetic substance is moved in a horizontal direction, the microbead outside the first opening OP1 can be inserted into the first opening OP1 by moving along the magnetic substance.

When the microbead is inserted into the first opening OP1, a voltage is applied to the first electrode 132 and the second electrode 136 to measure impedance of the microbead. The microbead has different impedances depending on the number of bound antibodies and proteins. The sensed impedance may be delivered to an external device such as a signal analyzer, etc., via the contact portion 138.

According to the present invention, size of electric field can be increased by using a sensor having a nanogap of 1 μm or less. Therefore, a very low concentration of the protein can be easily and reliably detected.

The biosensor may include an array in which a plurality of electrode pairs having the nanogaps are arranged. For example, the biosensor may include an array in which the electrode pairs having the nanogaps are arranged in 10×10, 20×20, 30×30, and the like.

Hereinafter, effects of the embodiments of the present invention will be described with reference to specific experimental examples.

Providing a Microbead Binding with a Protein Antibody

A tosylate-treated magnetic bead (Thermo Fisher, Dynabead M-280, diameter 2.8 μm, 14203) and a tau protein binding antibody (abcam, Anti-Tau (Phosphor S262) antibody, ab64193, 50 μl/250 μl) are inserted in a 0.1 M PBS buffer and placed in a 37° C. incubator, and incubated on a roll mixer for 24 hours.

Next, the magnetic bead bound to the tau protein binding antibody are washed with 0.4% Block ACE (AbD serotec, USA) and blocked with 0.2 M tris buffer. 30 mg/mL of the microbead solution was stored in PBST (Phosphate Buffered Saline with Tween-20, 0.01% Tween-20) containing 0.4% Block Ace.

Synthesis Example 1—Providing Microbead Binding with Tau Protein

The tau protein at a concentration of 5250 ng/mL was diluted 1/10 in various concentrations (0.5 fg/mL to 50 pg/mL) using 0.1% PBST. Tau protein was treated with Thiamet G, an O-glycosylation drug, if necessary.

The microbead bound to the tau protein binding antibody were diluted to 300 μl/ml using 0.1% PBST, and the tau protein (diluent) and the microbead (diluent) were mixed at a concentration of 1:2 and reacted in a refrigerator for 22 hours.

Next, the microbead bound to the tau protein is washed twice with 0.1% PBST and washed twice with PBS (Phosphate Buffered Saline). Thereafter, it is diluted to a bead concentration of 60 μl/ml using PBS.

Synthesis Example 2—Providing Microbead Binding with O-Glycosylated Antibody

A microbead (300 μl/ml) bound to tau protein were prepared in the same manner as in Synthesis Example 1.

The microbead is mixed with 10.4 ng of an antibody capable of binding O-glycosylated proteins (Cell signaling, O-GlcNAc (CTD110.6) Mouse mAB, #9875) and reacted in a refrigerator for 22 hours.

The microbead bound to the O-glycosylated tau-binding antibody is washed twice with 0.1% PBST, washed twice with PBS, and diluted to a bead concentration of 60 μl/ml using PBS.

Synthesis Example 3—Providing Microbead Binding with Phosphorylated Tau Antibody A microbead (300 μl/ml) bound to tau protein were prepared in the same manner as in Synthesis Example 1.

The microbead is mixed with 10 ng of an antibody capable of binding to phosphorylated tau protein (Thermo Fisher, Phospho-Tau (Ser202, Thr205) Antibody (AT8), MN1020) and reacted in a refrigerator for 22 hours.

The microbead bound to the phosphorylated tau-binding antibody is washed twice with 0.1% PBST, washed twice with PBS, and diluted to a bead concentration of 60 μl/ml using PBS.

The samples thus obtained were measured for impedance using a biosensor array (10×10 or 20×20) with an electrode interval of 0.7 μm. In the following table, PBS means PBS solution not containing microbead, Neg means a sample that does not bind to a tau protein but contains a microbead having only a protein binding antibody, BAT (bead-antibody-tau) means a sample containing microbead binding with tau protein, and BAT2(bead-antibody-tau-2nd_antibody) means a sample in which microbead binding with tau protein are treated with O-GlcNAc or AT8. In addition, impedance change rate is a value (%) obtained by dividing a difference between the impedance Zneg of Neg and the impedance BAT or BAT2 of divided by the impedance Zneg of Neg and multiplied by 100. Impedance change rate difference is defined as a value obtained by subtracting the impedance change rate of BAT from the impedance change rate of BAT2.

Table 1-1 below shows the impedance of samples not treated with Thiamet G for tau protein. Table 1-2 shows the impedance of samples treated with 100 uM Thiamet G for tau protein. The impedance change was measured by the concentration of tau protein.

TABLE 1-1

|  | BAT (MΩ) | BAT2 (MΩ) | Impedance change rate difference (%) |
|---|---|---|---|
| PBS | 213 | 213 | |
| Neg | 196 | 196 | |
| 0.5 fg/ml | 185 | 181 | 2.3 |
| 5.2 fg/ml | 177 | 165 | 5.9 |
| 52.4 fg/ml | 139 | 140 | −0.2 |
| 524 fg/ml | 127 | 116 | 5.6 |

TABLE 1-2

|  | BAT (MΩ) | BAT2 (MΩ) | Impedance change rate difference (%) |
|---|---|---|---|
| PBS | 220 | 220 | |
| Neg | 189 | 189 | |
| 0.5 fg/ml | 185 | 171 | 7.5 |
| 5.2 fg/ml | 168 | 130 | 20.4 |
| 52.4 fg/ml | 143 | 88.3 | 28.9 |
| 524 fg/ml | 126 | 63.8 | 32.8 |

Referring to Tables 1-1 and 1-2, when the concentration of Thiamet G was increased, that is, when O-glycosylation of tau protein was increased, it was confirmed that the impedance change rate difference for the microbead combined with O-glycosylated antibody was greatly increased. Therefore, it can be confirmed that increase or decrease of O-glycosylation of tau protein can be detected through this. In addition, even at very low tau protein concentrations, for example, 0.5 fg/ml, the impedance change rate difference can be seen.

Table 2-1 below shows impedance of a sample in which the microbead bound to Thiamet G-treated tau protein (0.5 pg/ml) is reacted with O-GlcNAc. Impedance change was measured by Thiamet G concentration (0 uM, 10 uM, 30 uM, 100 uM). Table 2-2 shows impedance of a sample in which the microbead bound to Thiamet G-treated tau protein (0.5 pg/ml) is reacted with AT8.

TABLE 2-1

|  | BAT (MΩ) | BAT2 (MΩ) | BAT-BAT2 (MΩ) | Impedance change rate difference (%) |
|---|---|---|---|---|
| PBS | 304.6 | 304.6 | | |
| Neg | 264.2 | 264.2 | | |
| 0 uM | 206.6 | 196.3 | 10.3 | 3.89 |
| 10 uM | 194.7 | 190.4 | 4.3 | 1.62 |
| 30 uM | 195.2 | 183.6 | 11.6 | 4.39 |
| 100 uM | 199.1 | 168.6 | 30.5 | 11.54 |

TABLE 2-2

|  | BAT (MΩ) | BAT2 (MΩ) | BAT-BAT2 (MΩ) | Impedance change rate difference (%) |
|---|---|---|---|---|
| PBS | 88.86 | 88.86 | | |
| Neg | 45.99 | 45.99 | | |
| 0 uM | 36.47 | 31.23 | 5.24 | 11.39 |
| 100 uM | 36.13 | 35.54 | 0.59 | 1.28 |

Table 3 below shows impedance difference between BAT and BAT2 (BAT−BAT2 or BAT2−BAT) for the impedance of Neg in Table 2-1 and Table 2-2, and ratio of impedance change due to phosphorylated tau (P) and O-glycosylated tau (O)

TABLE 3

| Thiamet G content | O ((BAT-BAT2)/Neg) | P ((BAT2-BAT)/Neg) | P/O |
|---|---|---|---|
| 0 uM | 0.0389 | 0.1139 | 14.552 |
| 100 uM | 0.1154 | 0.0128 | 0.111 |

Referring to Table 3, an increase in the concentration of Thiamet G may be regarded as an increase in O-glycosylated tau, that is, a decrease in phosphorylated tau. Thus, decrease in phosphorylated tau can be detected from decrease of the value of P/O.

Exemplary embodiments of the present invention may be used for monitor prognosis, course, treatment response, etc. of disease through protein detection. In addition, it can also be applied to a platform for developing therapeutic agents for diseases such as tauopathy.

The foregoing is illustrative and is not to be construed as limiting thereof. Although a few exemplary embodiments have been described, those skilled in the art will readily appreciate that many modifications are possible in the exemplary embodiments without materially departing from the novel teachings, aspects, and advantages of the invention. Accordingly, all such modifications are intended to be included within the scope of this disclosure.

What is claimed is:

1. A method for monitoring post-translational modifications of protein, the method comprising:
   providing multiple first microbeads, each of which formed by binding multiple protein antibodies to a surface of a base bead;
   providing multiple second microbeads by binding multiple target proteins to the multiple protein antibodies of the multiple first microbeads, each of the multiple second microbeads having a first post-translational modification or a second post-translational modification, which are inversely proportional to each other;
   forming third and fourth microbeads, respectively, by separately binding first and second post-translational antibodies to different second microbeads,
   wherein the first post-translational modification antibodies selectively bind to the first post-translational modification of the multiple target proteins to form the third microbeads;
   wherein the second post-translational modification antibodies selectively bind to the second post-translational modification of the multiple target proteins to form the fourth microbeads;
   measuring impedances of the third microbeads and the fourth microbeads, respectively; and
   obtaining a ratio of a first difference to a second difference, wherein the first difference is a difference between the impedances of the third microbeads and a reference impedance, and the second difference is a difference between the impedances of the fourth microbeads and the reference impedance.

2. The method of claim 1, wherein the multiple target proteins are tau proteins.

3. The method of claim 2, wherein the first post-translational modification is phosphorylated tau protein, and the second post-translational modification is O-glycosylated tau protein.

4. The method of claim 1, wherein the base bead is a magnetic bead.

5. The method of claim 1, wherein the reference impedance is impedance of the multiple first microbeads.

6. The method of claim 1, wherein the reference impedance is impedance of the multiple second microbeads.

7. The method of claim 1, wherein obtaining the ratio of the first difference to the second difference comprises:
   at a first time point, obtaining the ratio of the first difference to the second difference;
   at a second time point which is different from the first time point, obtaining the ratio of the first difference to the second difference; and
   comparing the ratio of the first time point with the ratio of the second time point.

8. The method of claim 1, wherein measuring the impedances of the third microbeads and the fourth microbeads is performed with the third microbeads or the fourth microbeads being disposed between a first electrode and a second electrode.

\* \* \* \* \*